United States Patent [19]

Chen et al.

[11] Patent Number: 5,221,732
[45] Date of Patent: Jun. 22, 1993

[54] ANTIMICROBIAL MAGAININ MODIFIED PEPTIDES

[75] Inventors: Hao-Chia Chen, Potomac, Md.; Judith H. Brown, Falls Church, Va.; John L. Morell; Charng-Ming Huang, both of Bethesda, Md.

[73] Assignee: The United States of America as represented by the Department of Health and Human Services, Washington, D.C.

[21] Appl. No.: 280,363

[22] Filed: Dec. 6, 1988

[51] Int. Cl.$^5$ .......................... C07K 7/08; C07K 7/10
[52] U.S. Cl. .................................... 530/326; 530/325; 530/327
[58] Field of Search .................. 530/325, 326, 327; 514/12-15

[56] References Cited

U.S. PATENT DOCUMENTS 4,810,777  3/1989  Zasloff .............................. 530/326

OTHER PUBLICATIONS

Zasloff et al., "Antimicrobial activity of Synthetic magainin peptides and several analogues", *Proc. Natl. Acad. Sci., USA*, vol. 85 pp. 910-913, Feb. 1988.

Primary Examiner—Lester L. Lee
Attorney, Agent, or Firm—Birch, Stewart, Kolasch & Birch

[57] ABSTRACT

Peptides which exhibit improved broad spectrum antimicrobial activity are designed and synthesized based on the peptide sequences of magainin or PGS peptides. The modified peptide analogues are synthesized by replacing low helical potential amino acid residues with high helical potential residues and modifying the two termini in order to enhance the amphiphilic structures as well as to prolong antimicrobial activity by lowering their susceptibility to protease degradation. For example, low propensity residues within a strategic region of magainin II, e.g. Ser$^8$, Gly$^{13}$ and Gly$^{18}$ are modified with Ala which is known to have high propensity. Amidation of Ser$^{23}$, and acylation of Gly$^1$ with acetyl or beta-alanyl and substitution of Gly$^1$ with beta-alanine are carried out in order to lower the susceptibility to exopeptidase action. A D-Ala modification for disrupting a stretch of the helical structure is also prepared so as to demonstrate the importance of an amphiphilic helical structure for antimicrobial activity. The modified peptide analogues exhibit an increase of up to two orders of magnitude in antimicrobial activity and, in the most favorable case, no appreciable increase in hemolytic activity over magainin 1.

13 Claims, 2 Drawing Sheets

ANTIMICROBIAL MAGAININ MODIFIED PEPTIDES

BACKGROUND OF THE INVENTION

1. Field of the Invention

The present invention relates to synthetic peptides and processes for synthesizing the same, wherein the peptides are designed and synthesized based on the peptide sequence of magainins or PGS peptides. More specifically, the present invention relates to modified peptide analogues of magainins or PGS peptides and processes for designing and synthesizing the same so as to enhance antimicrobial properties exhibited thereby.

2. Description of Related Art

A variety of peptides exhibiting antimicrobial properties have been isolated from the skin of the African clawed frog *Xenopus laevis*. Soravia et al, "Antimicrobial properties of peptides from Xenopus granular gland secretions." *Febs. Lett.*, 1988 Feb. 15, 228 (2), pp. 337–40. These peptides are secreted from the skin under stress and act as anti-infection agents and wound healing promoters. These peptides include a family of novel broad spectrum antimicrobial peptides known as magainins, also known as PGS peptides. Zasloff, "Magainins, a class of antimicrobial peptides from Xenopus skin: isolation, characterization of two active forms, and partial cDNA sequence of a precursor," *Proc. Natl. Acad. Sci. USA*, 1987 Aug., 84 (15), pp. 5449–53; Terry et al, "The cDNA sequence coding for prepro-PGS (prepro-magainins) and aspects of the processing of this prepro-polypeptide," *J. Biol. Chem.*, 1988 Apr. 25, 263 (12), pp. 5745–51. Magainins include two closely related peptides that each contain 23 amino acids and differ by two substitutions. These peptides are water soluble, nonhemolytic at their effective antimicrobial concentrations, and exhibit an alpha-helical structure with amphiphilic character. Marion et al, "A two-dimensional NMR study of the antimicrobial peptide magainin 2," *Febs Lett.*, 1988 Jan. 18, 227 (1), pp. 21–6. At low concentrations they inhibit the growth of numerous species of bacteria and fungi and induce osmotic lysis of protozoa. The sequence of a partial cDNA of the precursor reveals that the peptides derive from a common larger protein. These peptides appear to represent a previously unrecognized class of vertebrate antimicrobial activities.

Two magainins which have been isolated, i.e. magainin 1 and magainin 2, have been synthetically prepared and it has been demonstrated that the synthetic magainin peptides appear to be indistinguishable from the natural products with respect to chromatographic properties and biological activity. Zasloff et al, "Antimicrobial activity of synthetic magainin peptides and several analogues," *Proc. Natl. Acad. Sci. USA*. 1988 Feb., 85 (3), pp. 910–3. Although the antimicrobial properties exhibited by magainins are useful, it is desirable to improve these properties. The presence of amphiphilic structures in peptides, such as magainins, often leads to an ability to disrupt cell or organelle membranes or to form a channel affecting ion flux. These natural peptides, however, contain amino acid residues in the middle of the peptide chain having a low propensity for alpha-helical formation with amphiphilic structural characteristics. These peptides also appear to be susceptible to serum protease cleavage. Thus, the structural characteristics of magainins apparently reduce their potential for antimicrobial activity.

SUMMARY OF THE INVENTION

Therefore, it is an object of the present invention to provide synthetic Xenopus peptide analogues which exhibit improved antimicrobial activity.

It is a further object of the present invention to provide a process for designing and synthesizing peptide analogues which exhibit broad spectrum antimicrobial activity which is improved over that of the natural Xenopus peptides.

Another object of the present invention is to provide synthetic peptides based on modifications of the peptide sequence of magainins so as to enhance amphiphilic structural characteristics and antimicrobial properties.

Still, a further object of the present invention is to provide a process for designing and synthesizing magainin analogues so as to replace low helical potential amino acid residues with high helical potential residues and so as to modify the two termini in order to enhance the amphiphilic structures as well as to prolong antimicrobial activity by lowering their susceptibility to protease degradation.

The foregoing objects and others are accomplished in accordance with the present invention, generally speaking, by providing synthetic peptides which have a peptide sequence of amino acid residues and which comprise modified peptide analogues of magainin peptides, wherein said modified peptide analogues have the same peptide sequence as the magainin peptides except for modifications of the magainin peptide sequence which include substitutions of amino acid residues having a low propensity for helical formation with substitution residues having a high propensity for helical formation so as to lower susceptibility to exopeptidase action and so as to enhance amphiphilic structural characteristics and antimicrobial properties.

Further scope of the applicability of the present invention will become apparent from the detailed description and drawings provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention is further illustrated in the accompanying drawings wherein.

DETAILED DESCRIPTION OF THE INVENTION

Figure 1:
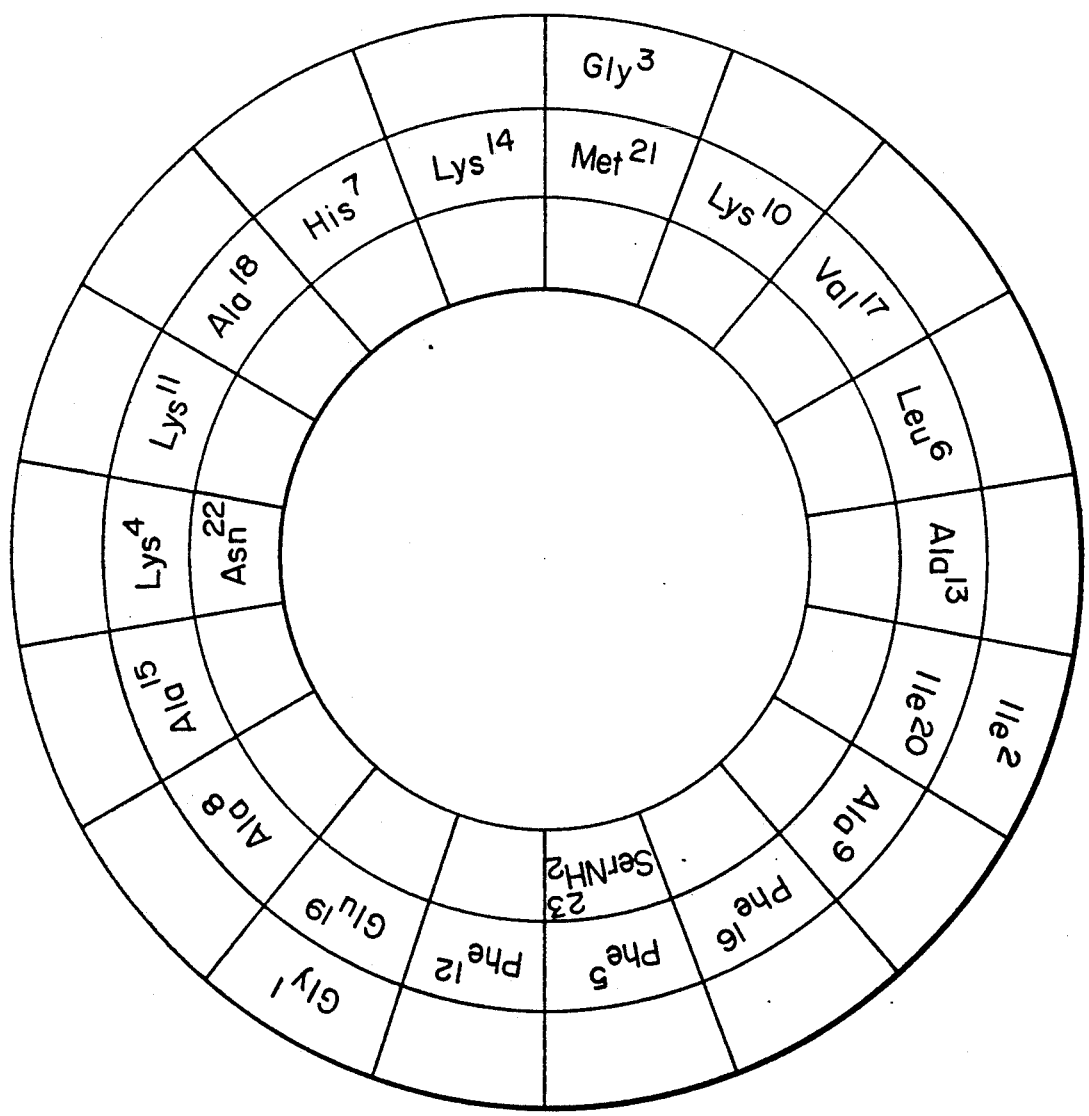
FIG. 1 is an alpha-helical wheel diagram of modified magainin analogue B.

The modified peptide analogues produced according to the present invention are based on the primary sequences of magainin peptides which have a high potential for alpha-helix formation based on calculations by the Chou-Fasman principles (Chou, P. Y. and Fasman, G. D. (1974) Biochemistry 13, 222–244). Projection of the helix by the Schiffer-Edmundson method (Schiffer, M. and Edmundson, A. B. (1967) Biophys. J. 7, 121–135) revealed it to be amphiphilic. The helical wheel diagram illustrated in FIG. 1 shows a modified peptide of the present invention (analogue B) which maintains an amphiphilic profile very similar to that of natural magainins. The depth of shading corresponds to the hydrophilicity values assigned by Hopp and Woods (Hopp T. P. and Woods, K. R. (1981) Proc. Natl. Acad. Sci USA 78, 3824–3828). Magainins 1 and 2 are preferred as structural peptide models for designing and synthesizing the modified peptide analogues of the present invention because of their broad spectrum antimicrobial activity. Magainin 2 is especially preferred because of its natural abundance and its higher antimicrobial activity than magainin 1. Synthetic magainins and modified analogues thereof may be prepared by using the standard Merrifield solid-phase method with benzhydrylamine resin and coupling procedures using symmetric anhydrides or active esters of t-butyloxycarbonyl amino acids as described, for example, in Morell, J. L. and Brown J. H. (1985) Int'l. J. Peptides Protein Research 26, 49–54. Purification may be accomplished by gel chromatography. Other methods of synthesis and purification known to those skilled in the art may also be employed.

In order to form the modified peptide analogues of the present invention so as to enhance amphiphilic structure and antimicrobial properties, it is preferred to substitute low helical propensity amino acid residues in strategic regions of the magainin structure with high helical propensity residues such as Ala, for example. Other amino acid residues which enhance amphiphilic structure may also be substituted. The two termini may be modified by amidation or acylation in order to stabilize helical conformation and lower susceptibility to exopeptidase action. For example, amidation and acylation of each of the termini with acetyl or beta-alanyl may be performed on the magainin structure.

EXAMPLES

In order to enhance the alpha-helical formation in the magainin structure, low propensity residues were modified within a strategic region of magainin 2, namely Ser[8], Gly[13] and Gly[18] with Ala which is known to have high propensity. Amidation of Ser[23], acylation of Gly[1] with acetyl or beta-alanyl and substitution of Gly[1] with beta-alanine were also carried out in order to lower the susceptibility to exopeptidase action. A D-Ala modification intended to disrupt a stretch of helical structure and thus to demonstrate the importance of an amphiphilic helical structure for the antimicrobial activity was also prepared.

Peptide Synthesis and Purification

Magainin 1 and eight peptides with the modifications cited above and designated as A, B, C, D, E, F, G, H (Table 1) were synthesized by the standard Merrifield solid-phase method with benzhydrylamine resin using symmetric anhydrides of t-butyloxycarbonyl amino acids as described by Morell and Brown. Anhydrous HF cleavage of the peptides from the resin after completion of the synthesis was performed according to the procedure described also by Morell and Brown. Purification of the peptide was accomplished by Sephadex G-25 gel chromatography followed by reverse-phase HPLC on a Vydac C4, 300 Å, 5 μm packing column with various eluting gradients composed of acetonitrile and 0.0 1M trifluoroacetic acid. In all cases, amino acid composition revealed theoretical recoveries of all amino acids within experimental error and HPLC peak integration at 215 nm indicated >93% purity of the products. Magainin 2 was synthesized by Applied Biosystems, Inc. (Foster City, Calif.) and was purified as above. Table 1 shows amino acid sequences of magainin 1, 2, and eight analogues designated A, B, C, D, E, F, G and H.

TABLE 1

Peptide sequence of magainins and analogues

| Peptide | Sequence |
|---|---|
| | 1      5      10      15      20      23 |
| Magainin 2 | G — I — G — K — F — L — H — S — A — K — K — F — G — K — A — F — V — G — E — I — M — N — S |
| Magainin 1 | — — — — — — — — — — — — — — — — — G — — — — — — — — — — — — — — — — — — — — — K — — |
| A | beta-A — — — — — — — — — — — — A — — — — — — — A — — — — — — — — A — — — — — — — NH₂ |
| B | — — — — — — — — — — — — — — — A — — — — — — — A — — — — — — — — A — — — — — — — NH₂ |
| C | N-Acetyl — — — — — — — — — — — A — — — — — — — A — — — — — — — — A — — — — — — — NH₂ |
| D | beta-A — — — — — — — — — — — — — — — — — — — — — A — — — — — — — — A — — — — — — — NH₂ |
| F | — — — — — — — — — — — — — — — — — — — — — — — A — — — — — — — — A — — — — — — — NH₂ |
| G | beta-A — — — — — — — — — — — — — — — — — — — — — A — — — — — — — — A — — — — — — — NH₂ |
| H | — — — — — — — — — — — — — — — a — — — — — — — a — — — — — — — — a — — — — — — — NH₂ |

All sequence modifications indicated are based on magainin 2.
One letter amino acid abbreviations are used as follows: beta-A = beta-alanine. a = D-alanine. G = glycine. K = lysine. F = phenylalanine. L = leucine. H = histidine, S = serine. A = alanine. V = valine. E = glutamic acid. I = isoleucine. M = methionine. and N = asparagine.

Circular Dichroic Measurements

In order to measure the amphiphilic structural characteristics of the modified peptides of the present invention, CD spectra were measured in either 50 mM potassium phosphate buffer, pH 7.0, or 40% (vol/vol) trifluoroethanol (Sigma) in 50 mM potassium phosphate buffer, pH 7.0, on a Jasco model J-5000A spectropolarimeter with a cell path length of 5 mm. Two scans per sample were performed over the wavelength range 250–200 nm. A statistical computer program developed by Provencher (Provencher, S. W. (1984) EMBL Technical Rep. DA07) was employed for the calculation of alpha-helical and beta-sheet contents.

CD of magainin 1, 2, and four analogues, B, C, F and G, were measured in aqueous phosphate buffer and 40% trifluoroethanol between the range 200 and 240 nm. The helical contents calculated from the CD spectra by the method of Provencher are summarized in table 2. It is apparent that both natural and modified peptides displayed no alpha-helix in the aqueous buffer. In the presence of 40% trifluoroethanol, all these peptides displayed an alpha-helical conformation indicating that a conformational change had occurred in a hydrophobic environment. There is no concentration dependence for the spectra of analogues detected after two-fold dilution. The alpha-helical contents of the two natural peptides are 24 and 26%, respectively, whereas the helical contents of the modified peptides are more than twice higher than those of the two natural peptides. The acetylation of Gly[1] did not appear to enhance the helical conformation.

TABLE 2

Circular dichroism of magainins and representative analogues

| | % structure calculated from CD spectra | | | |
|---|---|---|---|---|
| | 50 mM K-phosphate, pH7 | | 40% CF$_3$CH$_2$OH | |
| Peptides | alpha-helix | beta-sheet | alpha-helix | beta-sheet |
| Magainin 1 | 0 | 44 | 24 | 37 |
| Magainin 2 | 0 | 46 | 26 | 38 |
| B | 2 | 44 | 61 | 9 |
| C | 0 | 48 | 61 | 14 |
| F | 1 | 46 | 63 | 6 |
| G | 2 | 43 | 52 | 17 |

Antimicrobial Assay

The antimicrobial activities of magainin analogues were assayed by macrodilution broth procedure of Jones et al (Jones, R. N., Barry, A. L., Gaven, T. L. and Washington, J. A. in "Manual of Clinical Microbiology", Lennette, D. H. Balows, A., Hausler, W. J. and Shadomy, H. J., eds; fourth edition, American Society for Microbiology, Washington, D.C., 1985) with modifications. Different concentrations of peptides were added to 2 ml of trypticase soy broth (BBL) containing the inocula of the test organisms adjusted to $10^5$ and $10^6$ CFU/ml. Microbial growth was determined by the increase in OD$_{600}$, after incubation of the tubes at 35° C. for 6-9 h depending on the growth rate. The lowest concentration that resulted in complete inhibition of growth was recorded as the 100% minimal inhibitory concentration. The 50% minimal inhibitory concentration was determined from the plots of growth vs concentration of peptide.

Erythrocyte Hemolysis Assay

To 75×12 mm borosilicate test tubes containing a predetermined amount of dried peptide in duplicate, 2.5 ml of diluted human erythrocyte suspension (10%, v/v) in isotonic phosphate-buffered saline was added. After gentle mixing and incubation for 10 min at 37° C., tubes were centrifuged at 3000×g for 10 min. The supernatant was separated from cells and debris, diluted if necessary, and OD$_{350}$ measured. 100% hemolysis was obtained by using 0.1% Triton X-100.

Antimicrobial and Hemolytic Activities

The antimicrobial activity results are listed in Table 3. Analogues A, B, C, D, E, F and G are all active in growth inhibition of both Gram-positive and Gram-negative bacteria. The peptides with free alpha-amino groups are 20 to 240 times more active than either magainin 1 or 2. Acetylation of the alpha-amino group either maintains the same level of high activity or causes a small reduction in the case of Gram-positive bacteria, but causes significant reduction of growth inhibiting activity to the level of magainin 1 and 2 in the case of Gram-negative bacteria. The analogues displayed the same high activity against both beta-lactamase (+) and (−) Staphylococcus aureus. Peptide H whose alpha-helical structure is disrupted by D-Ala, however, showed no activity in all cases.

TABLE 3

Antimicrobial activity of magainin analogues assayed by macrodilution method
50% & 100%* Minimal inhibitory concentration, μg/ml

| Organism (ATCC#) | M1 | M2 | A | B | C | E | F | G | H |
|---|---|---|---|---|---|---|---|---|---|
| Escherichia coli | 100 | 50 | 1.2 | 1.2 | 10 | 1.2 | 1.2 | 2.5 | 70 |
| (25922) | 250 | 100 | 2.5 | 2.5 | 25 | 5 | 5 | 5 | >100 |
| Klebsiella pneumoniae | 100 | 100 | 5 | 5 | 60 | 5 | 5 | 10 | 100 |
| (13883) | 250 | 100 | 25 | 10 | 100 | 25 | 25 | 25 | >100 |
| Pseudomonas aeruginosa | 430 | >100 | 15 | 15 | >100 | 25 | 25 | 25 | 100 |
| (27853) | >500 | >100 | 25 | 25 | >100 | 50 | 50 | 100 | >100 |
| Streptococcus agalactiae | 60 | 50 | 0.25 | 0.25 | 0.5 | 0.25 | 0.25 | 0.5 | 100 |
| (12386) | 75 | 100 | 1 | 1 | 1 | 1 | 1 | 2.5 | >100 |
| Streptococcus faecalis | 360 | >100 | 5 | 5 | 5 | 10 | 10 | 10 | >100 |
| (29212) | >500 | >100 | 10 | 10 | 25 | 25 | 25 | 50 | >100 |
| Staphylococcus aureus (29213) | 500 | >100 | 5 | 5 | 7.5 | 5 | 5 | 5 | >100 |
| beta-lactamase(+) | >500 | >100 | 10 | 10 | 25 | 10 | 10 | 10 | >100 |
| Staphylococcus aureus (25923) | 360 | >100 | 5 | 5 | 10 | 10 | 10 | 10 | >100 |
| beta-lactamase(−) | >500 | >100 | 10 | 10 | 25 | 25 | 25 | 25 | >100 |

M1 and M2 are synthetic magainin 1 and 2, respectively.
*Minimal level of 100% inhibition is indicated in bold number.
>denotes no activity detected at the dose indicated.

Figure 2:
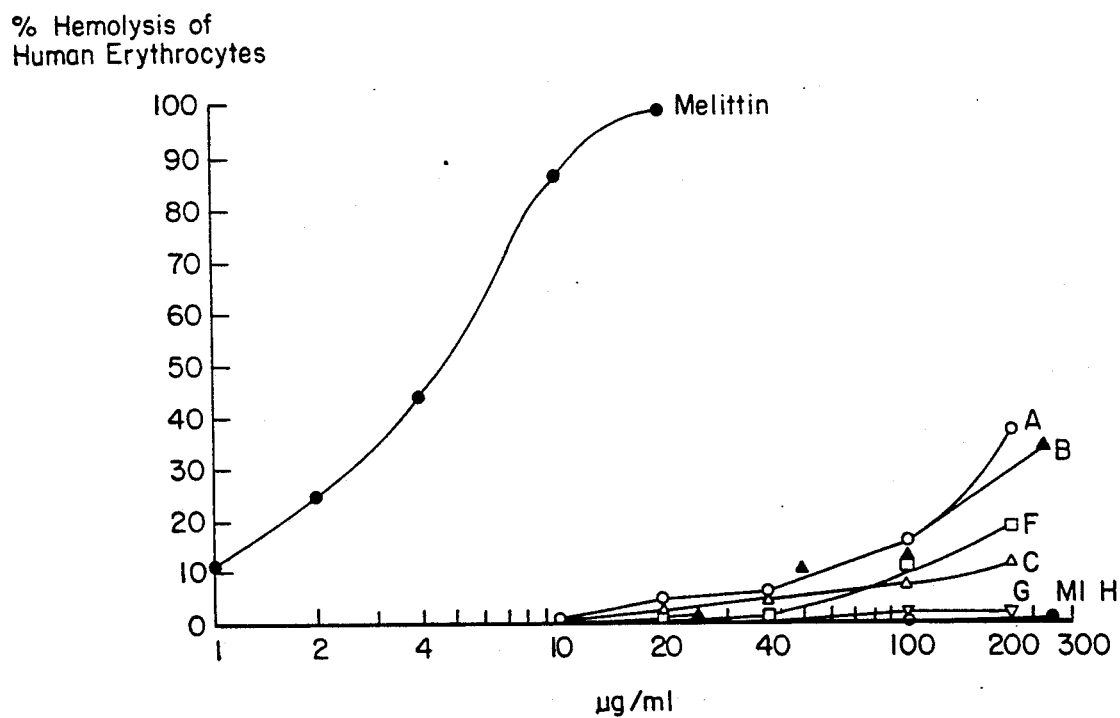
FIG. 2 is a graph showing hemolytic activities of melittin, magainin 1, and modified peptide analogues of the present invention.

Human erythrocyte hemolytic activity was measured for magainin 1 and analogues A, B, C, F, G and H in comparison with the hemolytic principle, melittin, from honey bee venom. The result is illustrated in FIG. 2. Neither magainin 1 nor analogue H showed hemolytic activity at 250 μg/ml of heparinized blood. At a peptide concentration of 500 μg/ml (not shown), analogue H did not cause hemolysis whereas magainin 1 showed only 3% hemolysis. However, the other analogues exhibited appreciable hemolysis at 100 μg/ml which was approximately equivalent to 1/100 the potency of melittin. Analogue G showed less than 1% hemolytic activity at 200 μg/ml. These results indicate that the hemolytic activity of the analogues generally increased in parallel to the increase of growth inhibitory activity except in the case of analogue G which showed high antimicrobial activity but exceptionally low hemolytic activity.

Omission of replacement at Ser$^8$ reduced the antimicrobial activity of analogues E, F and G only slightly. These derivatives (F and G) also displayed, as mentioned above, a lower hemolytic activity which also increases their potential therapeutic value. Acetylation of the alpha-amino terminus (analogue C) significantly reduced the growth inhibitory activity toward Gram-negative bacteria but the reduction toward Gram-positive bacteria (Table 3) was less despite the observation that the proportions of alpha-helical and apparent beta-sheet structures were identical to its non-acetylated counterpart (analogue B). Elongation or substitution with beta-alanine at the amino-terminus had no effect on either potency or specificity. These findings suggest that not only enhancement of the alpha-helical structure is essential but also a free alpha-amino terminus is required to elicit the maximal antimicrobial activity.

Collectively, various magainin analogues have been synthesized which have increased propensity to form amphiphilic alpha-helical structure and display one to two order increases of antimicrobial activity. Because of high antimicrobial potency, these new series of magainin analogues have a great value in the treatment of bacterial and fungal infections in man and domestic animals.

The invention being thus described, it will be obvious the same may be varied in many ways. Such variations are not to be regarded as a departure from the spirit and scope of the invention and all such modifications as would be obvious to one skilled in the art are intended to be included within the scope of the following claims.

What is claimed is:

1. A synthetic peptide which has a peptide sequence of amino acid residues and which comprises a modified peptide analogue of a magainin peptide, wherein said modified peptide analogue has the same peptide sequence as said magainin peptide except for modifications of the magainin peptide sequence which comprise amidation of the magainin peptide carboxyl-terminus and substitutions of amino residues having a low propensity for helical formation with substitution residues having a high propensity for helical formation so as to lower susceptibility to exopeptidase action and so as to enhance amphiphilic structural characteristics and antimicrobial properties.

2. The synthetic peptide of claim 1, wherein said magainin peptide sequence modifications comprise substitution of alanine at positions 8,13 and 18 in the peptide sequence.

3. The synthetic peptide of claim 1, wherein said magainin peptides sequence modifications comprise substitution of beta-alanine at position 1 and substitution of alanine at positions 13 and 18 in the peptide sequence.

4. The synthetic peptide of claim 1, wherein said magainin peptide sequence modifications comprise substitution of alanine at positions 13 and 18 in the peptide sequence, and addition of beta-alanine to the magainin peptide amino-terminus.

5. The synthetic peptide of claim 1, wherein the peptide sequence thereof comprises: (beta-A)-I-G-K-F-L-H-A-A-K-K-F-A-K-A-F-V-A-E-I-M-N-S-NH$_2$ wherein beta-A is beta-alanine.

6. The synthetic peptide of claim 1, wherein the peptide sequence thereof comprises: G-I-G-K-F-L-H-A-A-K-K-F-A-K-A-F-V-A-E-I-M-N-S-NH$_2$.

7. The synthetic peptide of claim 1, wherein the peptide sequence thereof comprises: (N-Acetyl)-G-I-G-K-F-L-H-A-A-K-K-F-A-K-A-F-V-A-E-I-M-N-S-NH$_2$.

8. The synthetic peptide of claim 1, wherein the peptide sequence thereof comprises: (beta-A)-G-I-G-K-F-L-H-A-A-K-K-F-A-K-A-F-V-A-E-I-M-N-S-NH$_2$ wherein beta-A is beta-alanine.

9. The synthetic peptide of claim 1, wherein the peptide sequence thereof comprises: (beta-A)-I-G-K-F-L-H-S-A-K-K-F-A-K-A-F-V-A-E-I-M-N-S-NH$_2$ wherein beta-A is beta-alanine.

10. The synthetic peptide of claim 1, wherein the peptide sequence thereof comprises: G-I-G-K-F-L-H-S-A-K-K-F-A-K-A-F-V-A-E-I-M-N-S-NH$_2$.

11. The synthetic peptide of claim 1, wherein the peptide sequence thereof comprises: (beta-A)-G-I-G-K-F-L-H-S-A-K-K-F-A-K-A-F-V-A-E-I-M-N-S-NH$_2$ wherein beta-A is beta-alanine.

12. The synthetic peptide of claim 1, wherein the peptide sequence thereof comprises: G-I-G-K-F-L-H-S-a-K-K-F-a-K-A-F-V-a-E-I-M-N-S-NH$_2$.

13. The synthetic peptide of claim 1, wherein said magainin peptide sequence modifications comprise substitution of alanine at positions 13 and 18 in the peptide sequence and acetylation of the magainin peptide amino-terminus.

* * * * *